United States Patent [19]

Kanai et al.

[11] Patent Number: 5,157,075
[45] Date of Patent: Oct. 20, 1992

[54] MODIFIED MELANIN

[75] Inventors: Hirokazu Kanai, Mobara; Yuji Inada, 1-808, Tamagawa-Haimu, 24-10, Shimomaruko 2-chome, Ota-ku, Tokyo, both of Japan

[73] Assignees: Taenaka Mining Co., Ltd.; Yuji Inada, both of Japan

[21] Appl. No.: 687,993

[22] Filed: Apr. 19, 1991

[30] Foreign Application Priority Data

May 2, 1990 [JP] Japan ................................ 2-115150

[51] Int. Cl.$^5$ ..................... C08L 89/00; C08G 69/48
[52] U.S. Cl. ..................................... 525/54.1; 524/17; 528/425
[58] Field of Search ......................................... 525/54.1

[56] References Cited

U.S. PATENT DOCUMENTS 4,855,144  8/1989  Leong et al. .................. 424/487
5,047,447  9/1991  Gallas ........................... 523/106

Primary Examiner—Joseph L. Schofer
Assistant Examiner—Wu C. Cheng
Attorney, Agent, or Firm—Jordan B. Bierman

[57] ABSTRACT

Melanin modified with a polyethylene glycol derivative becomes soluble in water and an organic solvent, and can be applied widely to cosmetics, medicines and dyes.

12 Claims, 1 Drawing Sheet

MODIFIED MELANIN

BACKGROUND OF THE INVENTION

This invention relates to a modified melanin soluble in an organic solvent and water.

Melanin is a black dye existing in skins, eyes, hairs and feathers of animals, ink of the Cephalopoda, and fruits and seeds of plants.

Melanin is insoluble in water and almost all organic solvents, and also insoluble in acids other than hot concentrated sulfuric acid.

Thus, if melanin can be solubilized in water or an organic solvent, it will be utilized easily and can be applied variously. For example, such melanin is expected to be used as a hair dye or a dye by utilizing it as a black dye, an anti-suntan cosmetic and an ultraviolet-screening material of home and vehicular windowpanes by utilizing its effect of absorbing UV rays, and a medicine for rheumatism by utilizing its action of making peroxide non-toxic.

T.G. Bonner et al. found that an amino group existed in melanin by measuring infrared spectroscopic spectra of various melanins (Infra-Red Spectra of Some Melanins, NATURE, Vol. 194, 1078, (1962)). The present inventors also quantitated an amino group according to the trinitrobenzenesulfonate (TNBS) method in addition to measurement of infrared spectra of isolated melanins, and proved that about 8 amino groups existed in one molecule of melanin (calculated as molecular weight of melanin:14,000).

SUMMARY OF THE INVENTION

The present inventors have attempted to solubilize melanin in water or an organic solvent by chemically modifying amino groups possessed by melanin.

The present inventors have investigated intensively, and consequently found that melanin can be solubilized by modifying amino groups of melanin by a polyethylene glycol derivative, to accomplish the present invention.

The present invention is concerning a soluble modified melanin modified by polyethylene glycol derivatives.

BRIEF DESCRIPTION OF THE DRAWING

Closed circles relate to the recovery of PEG melanin extracted. Open circles relate to the number of amino groups per melanin molecule.

DESCRIPTION OF THE PREFERRED EMBODIMENTS

Figure 1:
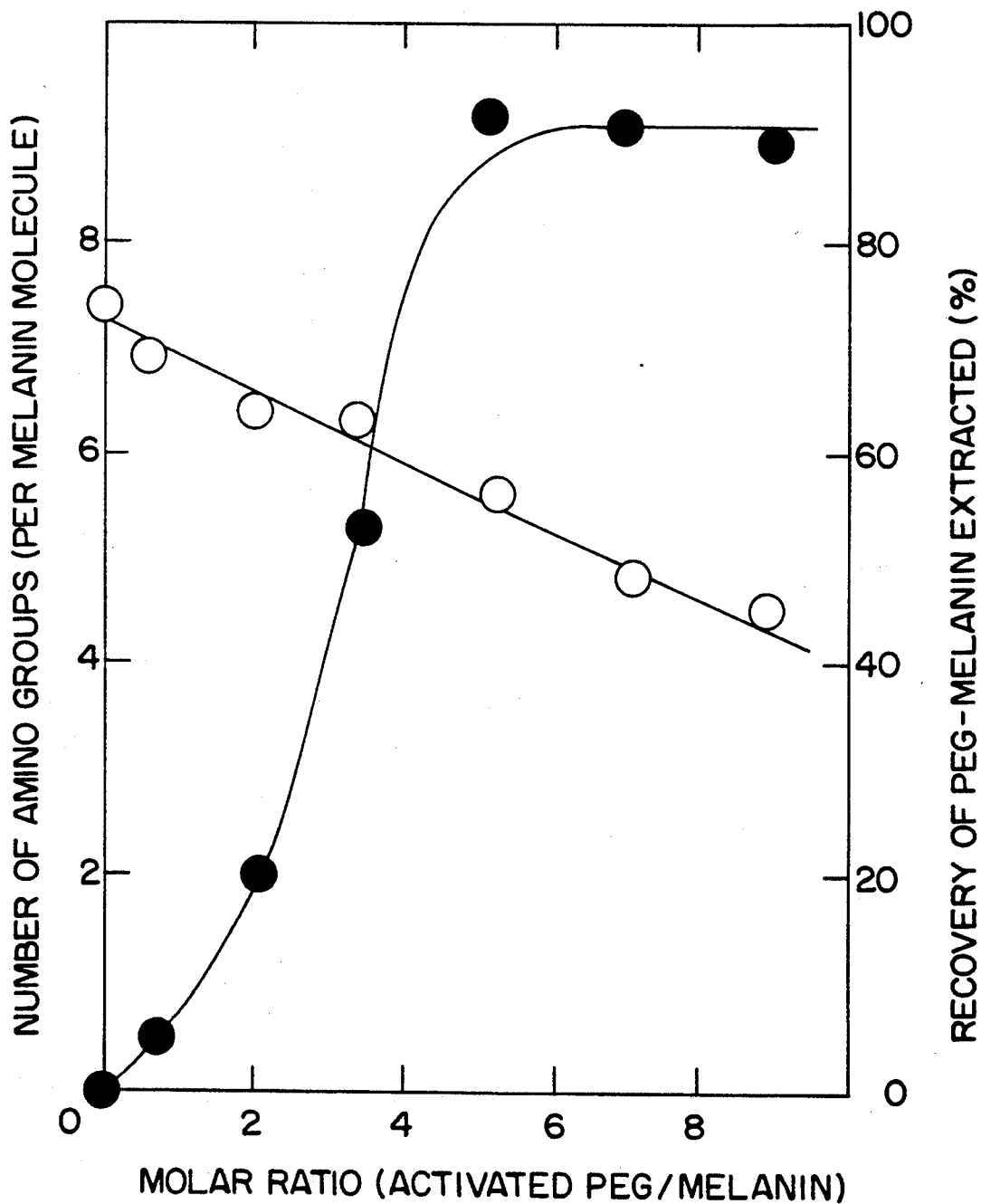
FIG. 1 is a graph showing the amount of activated PEG added to a purified melanin and the recovery of a PEG-melanin extracted.

Melanin modified by a polyethylene glycol derivative becomes more soluble as its modification rate becomes higher. When two or more amino groups among 8 amino groups are modified, melanin becomes soluble in almost all solvents in which polyethylene glycol is soluble.

For solubilizing melanin, polyethylene glycol having a molecular weight of 1,000 to 50,000 is used. One end of the polyethylene glycol derivative is substituted with a hydrophobic group including an alkyl group such as methyl, an aryl group such as phenyl and tolyl, an aralkyl group such as benzyl, and an acyl group such as acetyl. Further, the polyethylene glycol derivative may be a copolymer of polyoxyethylene allyl ether and maleic anhydride. For preparing a modified melanin by using such a polyethylene glycol derivative, for example, an activated PEG is prepared according to the following methods and reacted with melanin to bond thereto.

Method A: A method of using 2,4-bis(methoxypolyoxyethylene)-6-chloro-S-triazine or 2-methoxypolyoxyethylene-4,6-dichloro-S-triazine which is an activated PEG obtained by reacting monomethoxypolyethylene glycol with cyanuric chloride.

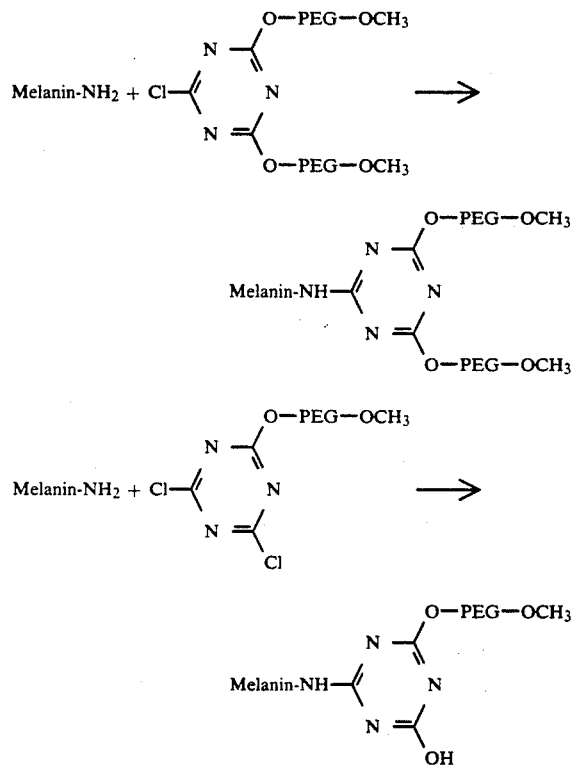

Method B: A method of using an activated PEG obtained by reacting α-carboxymethyl-ω-methoxy polyethylene glycol with N-hydroxysuccinimide by using a carbodiimide reagent such as dicyclohexylcarbodiimide.

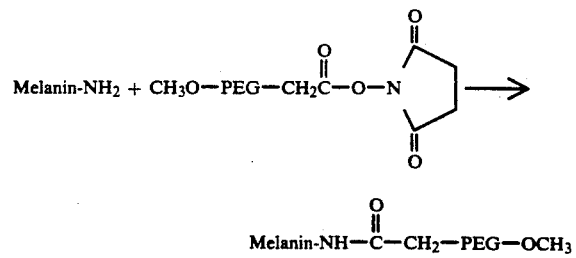

Method C: A method of using an activated PEG obtained by reacting monomethoxy polyethylene glycol with succinic anhydride and then with N-hydroxysuccinimide by using a carbodiimide reagent such as dicyclohexylcarbodiimide.

Melanin-NH$_2$ +

-continued

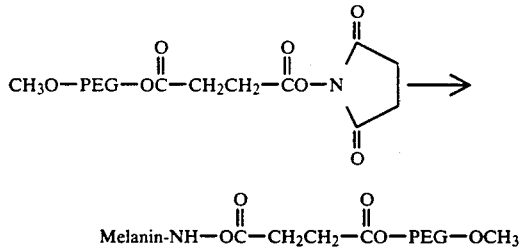

Method D: A method of using activated PEG obtained by copolymerizing polyoxyethylene allyl ether and maleic anhydride.

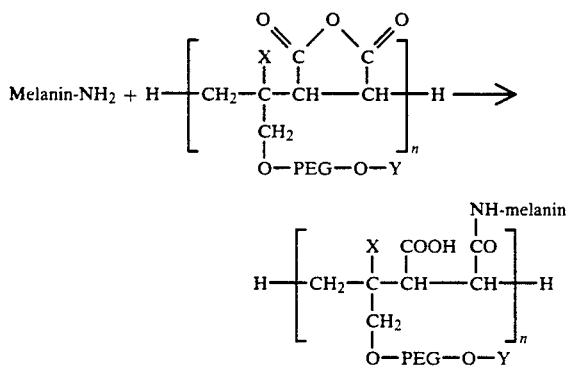

In the formulae, X represents a hydrogen atom or a methyl group. Y represents an alkyl group, an aryl group, an aralkyl group or an acyl group, n represents 2 to 200.

EXAMPLES

Examples are shown below, but the present invention is not limited to these embodiments.

Reference example 1:

Isolation of melanin (1)

Hairs of human beings and feathers of animals were hydrolyzed by an inorganic acid, and amino acid in a decomposed material was separated. Thereafter, a black residue was dissolved in alkali (e.g. potassium hydroxide) for several hours, and insolubles were removed by filtration. Subsequently, inorganic acid was added to the solution (black) to precipitate a (crude) melanin on an acid side. Then, the crude melanin was dissolved by adding a concentrated sulfuric acid, and after dissolution, insolubles were removed by filtration. The solution after filtration was added dropwise in a large amount of water to precipitate melanin. The precipitates were washed with water and then washed with alcohol for removing fats and oils thereform, followed by drying, to obtain a purified melanin (1). The purified melanin (1) had the following physical properties.

Appearance: Blackish brown powder.
Molecular weight: 14,000.
Constitutional elements: C: 58.0, H: 6.4, 0: 24.2, N: 4.6 and S: 4.7 %.

Reference example 2:

Isolation of melanin (2)

From ink sacs of 5 squids (*Todarodes pacificus*), about 10 ml of ink was taken out, washed with 200 ml of water, followed by 200 ml of 1% hydrochloric acid. Then, 50 ml of concentrated hydrochloric acid was added to hydrolize at 105° C. for 72 hours. The ink was washed with water until the filtrate became neutral to obtain 0.5 g of precipitates.

Subsequently, 10 ml of dimethylsulfoxide was added to the resulting precipitates, and the mixture was stirred at 40° C. for 2 hours to dissolve the precipitates. The solution obtained was subjected to centrifugation (7,000 rpm) for 20 minutes to remove insolubles, and then 30 ml of acetone was added thereto to prepicitate melanin. The melanin was subjected to centrifugation (7,000 rpm) for 10 minutes to obtain melanin precipitates, and then the melanin precipitates obtained were washed with acetone, followed by drying under reduced pressure, to obtain 0.4 g of a purified melanin (2). The purified melanin (2) had the following physical properties.
Appearance: Blackish brown amorphous powder.
Ash content: <0.3 %.

EXAMPLE 1

After dissolving 1 g of the purified melanin (1) in 50 ml of a 0.2M sodium borate buffer (pH 10), 10 g of activated PEG [Method A, 2,4-bis(methoxypolyoxyethylene)-6-chloro-S -triazine] (molecular weight of PEG: 5,000×2) was added to the solution, and the mixture was reacted at 37° C. for 20 hours. The reaction mixture was poured into 300 ml of a separatory funnel, and 200 ml of chloroform and 10 g of NaCl were added therein. The separating funnel was shaken for about 5 minutes to extract a PEG-melanin (1) with a solvent, and then a chloroform layer at the lower portion was separated and recovered. Further, to the remaining upper layer were added 200 ml of chloroform and 10 g of NaCl, and the funnel was shaken for about 5 minutes and then left to stand to recover a chloroform layer. This chloroform layer was combined with the above chloroform layer. To this extract was added hexane to precipitate PEG-melanin (1). At this time, for removing unreacted PEG as much as possible, the amount of hexane to be added was made 1.9 to 2.0 times (V/V) of the chloroform extract. After these precipitates were separated by filtration, 100 ml of chloroform was added to dissolve PEG-melanin (1). Hexane was added again to the solution to precipitate PEG-melanin (1).

The precipitates were filtered and then subjected to drying under reduced pressure to remove the solvent. For removing salts, the dried product was subjected to dialysis and then lyophilized to obtain PEG-melanin (1). The amount recovered was 2.5 g (yield of melanin: 90%).

The PEG-melanin (1) had the following physical properties.
(1) Appearance: Blackish brown.
(2) Molecular weight: 45,000.
(3) Amino group: 5 groups/one molecule of melanin (calculated as molecular weight of melanin 14,000).
(4) Amount: Melanin 36%, PEG 64%.

The solubilities of the melanin and the PEG-melanin (1) were measured by using water, alcohol, chloroform and other solvents shown in Table 1. Specifically, each 4 g of melanin and modified melanin was added in 5 ml of the respective solvents, and each mixture was stirred and dispersed for 10 minutes, and centrifuged to separate a solution and precipitates (3,500 rpm, 10 minutes). 2 ml of the dissolved solution was dispensed, and the solvent was removed under reduced pressure. To the residue was added 3 ml of DMSO to dissolve the residue completely. The absorbance of the solution obtained was measured by using a spectrophotometer at a wavelength of 460 nm.

The solubilities of the melanin and the PEG-melanin (1) to the respective solvents is shown in Table 1.

TABLE 1

(4 mg of sample is added in 5 ml of solvent)

| Solvent | Solubility (%) | |
|---|---|---|
| | PEG-Melanin(1) | Melanin |
| DMSO | 100 | 100 |
| DMF | 100 | 50 |
| Water | 100 | 0 |
| Ethyl alcohol | 100 | 0 |
| Acetone | 45 | 0 |
| Chloroform | 100 | 0 |
| Benzene | 80 | 0 |
| Pyridine | 90 | 20 |
| Dioxane | 100 | 0 |

EXAMPLE 2

The relationship between the amount of an activated PEG [2,4-bis(methoxypolyoxyethylene)-6-chloro-S-triazine] added to the purified melanin (1) and the amount of melanin extracted with chloroform after reaction was examined according to the same method as in Example 1. After 400 mg of the purified melanin (1) was dissolved in 20 ml of a 0.2M sodium borate buffer (pH 10), to each 2 ml of the dissolved solution dispensed was added an activated PEG in an amount of 0, 20, 120, 200, 300, 400 and 500 mg, respectively. After reacting at 37° C. for 20 hours, an amino group was determined according to the TNBS (trinitrobenzenesulfonate) method, and solvent extraction was carried out by using chloroform. The amount of the PEG-melanin transferred into a chloroform layer was determined by measuring an absorbance at a wavelength of 460 nm by a spectrophotometer. The results are shown in FIG. 1.

EXAMPLE 3

0.5 g of the purified melanin (1) was dissolved in 25 ml of a 0.2M sodium borate buffer (pH 8). After dissolution, 5 g of an activated PEG obtained by the above Method B was added, and the mixture was reacted at 37° C. for 20 hours. After the reaction, extraction with chloroform, precipitation with hexane, dialysis and drying were carried out in the same manner as in Example 1 to obtain a PEG-melanin (2).

The PEG-melanin (2) had the following physical properties.
Amount recovered: 1.5 g.
Appearance: Blackish brown powder.
Solubility: Similar to those in Example 1.

EXAMPLE 4

0.5 g of the purified melanin (1) was dissolved in 25 ml of a 0.2M sodium borate buffer (pH 8). After dissolution, 5 g of the activated PEG obtained by the above Method C was added, and the mixture was reacted at 37° C. for 20 hours. After the reaction, extraction with chloroform, precipitation with hexane, dialysis and drying were carried out in the same manner as in Example 1 to obtain a PEG-melanin (3).

The PEG-melanin (3) had the following physical properties.
Amount recovered: 1.2 g.
Appearance: Blackish brown powder.
Solubility: Similar to those in Example 1.

EXAMPLE 5

0.5 g of the purified melanin (1) was dissolved in 25 ml of a 0.2M sodium borate buffer (pH 8.5). After dissolution, 5 g of a copolymer of polyoxyethylene allyl ether and maleic anhydride obtained by the above Method D (where X is a hydrogen atom, Y is a methyl group, n is 8, and the molecular weight is 13,000) was added, and the mixture was reacted at 37° C. for 20 hours. After the reaction, extraction with chloroform, precipitation with hexane, dialysis and drying were carried out in the same manner as in Example 1 to obtain a PEG-melanin (4).

The PEG-melanin (4) had the following physical properties.
Amount recovered: 1.0 g.
Appearance: Blackish brown powder.
Solubility: shown in the following Table 2 which was determined by the same manner as in Example 1.

TABLE 2

| Solvent | Solubility (%) PEG-Melanin(4) |
|---|---|
| DMSO | 100 |
| DMF | 100 |
| Water | 100 |
| Ethyl alcohol | 100 |
| Acetone | 30 |
| Chloroform | 100 |
| Benzene | 40 |
| Pyridine | 90 |
| Dioxane | 20 |

As clearly seen from the above Table 1 and Table 2, the melanins modified by the polyethylene glycol derivatives of the present invention became soluble in water and organic solvents, whereby the modified melanin of the present invention can be applied to cosmetics, medicines and dyes.

We claim:

1. A soluble melanin comprising melanin reacted with a polyethylene glycol compound wherein the polyethylene glycol derivative is 2,4-bis(methoxypolyoxyethylene)-6-chloro -S-triazine or 2-methoxypolyoxyethylene-4,6-dichloro-S-triazine.

2. A soluble melanin comprising melanin reacted with a polyethylene glycol compound wherein the polyethylene glycol derivative is an activated PEG obtained by reacting α-carboxymethyl-ω-methoxypolyethylene glycol with N-hydroxysuccinimide by using a carbodiimide reagent.

3. A soluble melanin comprising melanin reacted with a polyethylene glycol compound wherein the polyethylene glycol derivative is an activated PEG obtained by reacting monomethoxypolyethylene glycol with succinic anhydride and then N-hydroxysuccinimide by using a carbodiimide reagent.

4. A soluble melanin comprising melanin reacted with a polyethylene glycol compound wherein the polyethylene glycol derivative is a copolymer of polyoxyethylene allyl ether and maleic anhydride.

5. A soluble melanin comprising melanin reacted with a polyethylene glycol compound wherein said polyethylene glycol compound has a molecular weight of 1000 to 50,000.

6. A soluble melanin comprising melanin reacted with a polyethylene glycol compound wherein said compound contains a hydrophobic group at one end thereof.

7. A soluble melanin comprising melanin reacted with a polyethylene glycol compound wherein said compound is a copolymer of polyoxyethylene alkyl ether and maleic anhydride.

8. The melanin according to claim 1, wherein 2,4-bis(-methoxypolyoxyethylene)-6-chloro-S -triazine or 2-methoxypolyoxyethylene-4,6-dichloro-S -triazine is prepared by reacting a monomethoxypolyethylene glycol and cyanuric chloride.

9. The melanin according to claim 2, wherein the carbodiimide reagent is dicyclohexylcarbodiimide.

10. The melanin according to claim 3, wherein the carbodiimide reagent is dicyclohexylcarbodiimide.

11. The melanin of claim 6, wherein said hydrophobic group is alkyl, aryl, aralkyl, or acyl.

12. The melanin of claim 11 wherein said hydrophobic group is selected from the class consisting of methyl, phenyl, tolyl, benzyl, and acetyl.

* * * * *